(12) United States Patent
Merritt

(10) Patent No.: US 11,597,688 B1
(45) Date of Patent: Mar. 7, 2023

(54) PROCESS FOR MAKING A FULLY WATER-SOLUBLE GRANULE COMPRISING HUMIC ACID AND A MICROBIAL COMMUNITY COMPOSITION

(71) Applicant: Kevin Merritt, St. Johns, FL (US)

(72) Inventor: Kevin Merritt, St. Johns, FL (US)

(73) Assignee: HUMIC GROWTH SOLUTIONS, LLC, Jacksonville, FL (US)

(*) Notice: Subject to any disclaimer, the term of this patent is extended or adjusted under 35 U.S.C. 154(b) by 0 days.

(21) Appl. No.: 16/814,539

(22) Filed: Mar. 10, 2020

Related U.S. Application Data

(60) Division of application No. 15/878,773, filed on Jan. 24, 2018, now Pat. No. 10,597,337, which is a continuation-in-part of application No. 14/738,865, filed on Jun. 13, 2015, now Pat. No. 9,914,670.

(60) Provisional application No. 62/013,789, filed on Jun. 18, 2014.

(51) Int. Cl.
   C05F 11/08     (2006.01)
   C05F 11/02     (2006.01)
   C12N 1/20      (2006.01)

(52) U.S. Cl.
   CPC .............. C05F 11/08 (2013.01); C05F 11/02 (2013.01); C12N 1/20 (2013.01)

(58) Field of Classification Search
   CPC ............. C05F 11/08; C05F 11/02; C12N 1/20
   See application file for complete search history.

(56) References Cited

U.S. PATENT DOCUMENTS

| | | |
|---|---|---|
| 2,992,093 A | 7/1961 | Burdick |
| 3,700,728 A | 10/1972 | Moschopedis et al. |
| 3,932,166 A | 1/1976 | Vignovich et al. |
| 4,015,972 A | 4/1977 | Watkins et al. |
| 4,459,149 A | 7/1984 | Moran et al. |
| 5,026,416 A | 6/1991 | Alexander |
| 5,034,045 A | 7/1991 | Alexander |
| 5,876,479 A | 3/1999 | Hedgpeth |
| 6,783,567 B1 | 8/2004 | Waters |
| 8,388,722 B2 | 3/2013 | Lynch et al. |
| 9,914,670 B1 | 3/2018 | Merritt |
| 10,597,337 B1 | 3/2020 | Merritt |
| 10,723,667 B1 | 7/2020 | Merritt |

(Continued)

FOREIGN PATENT DOCUMENTS

| | | |
|---|---|---|
| CN | 1026095 C | 10/1994 |
| CN | 101024590 B | 11/2010 |

(Continued)

OTHER PUBLICATIONS

Granular Myco (GreenGro Biologicals) <https://www.thegreengro.com/product/granular-myco/> Oct. 23, 2017 (Year: 2017).*

(Continued)

*Primary Examiner* — Jennifer A Smith
(74) *Attorney, Agent, or Firm* — Gray Ice Higdon

(57) ABSTRACT

Disclosed is a process for making a fully water-soluble granule comprising humic acid and a microbial community composition. Disclosed also is a fully water-soluble granule comprising humic acid and a microbial community composition. Such a granule is useful as an organic aid to crop growth, particularly in applications where solubility is desirable or necessary.

10 Claims, 2 Drawing Sheets

(56) References Cited

U.S. PATENT DOCUMENTS

| | | |
|---|---|---|
| 11,117,840 B1 | 9/2021 | Merritt |
| 11,136,275 B2 | 10/2021 | Merritt |
| 11,136,505 B2 | 10/2021 | Merritt |
| 2005/0039509 A1 | 2/2005 | Muma |
| 2008/0216534 A1 | 9/2008 | Karr |
| 2011/0259067 A1 | 10/2011 | Lynch |
| 2013/0239633 A1 | 9/2013 | Halos |
| 2016/0200634 A1 | 7/2016 | Zaseybida |
| 2016/0229761 A1 | 8/2016 | Cherry |
| 2017/0334795 A1 | 11/2017 | Cherry |
| 2018/0311712 A1 | 11/2018 | Le |
| 2020/0148952 A1 | 5/2020 | Merritt |
| 2020/0270183 A1 | 8/2020 | Merritt |
| 2021/0323988 A1 | 10/2021 | Merritt |
| 2022/0017824 A1 | 1/2022 | Merritt |
| 2022/0204421 A1 | 6/2022 | Merritt |

FOREIGN PATENT DOCUMENTS

| | | |
|---|---|---|
| CN | 101905983 A | 12/2010 |
| CN | 202148263 U | 2/2012 |
| CN | 102718605 A | 10/2012 |
| CN | 101768019 B | 12/2012 |
| CN | 102898254 A | 1/2013 |
| CN | 102942417 A | 2/2013 |
| CN | 101935243 B | 7/2013 |
| CN | 102875248 B | 10/2014 |
| CN | 104892296 A | 9/2015 |
| CN | 107746331 A | 3/2018 |
| CN | 109485501 A | 3/2019 |
| CN | 110734334 A | 1/2020 |
| EP | 1216976 A2 | 6/2002 |
| IN | 02359CH2010 | 9/2010 |
| RU | 2443663 C1 | 2/2012 |
| RU | 2491266 C1 | 1/2013 |
| WO | 9533702 A1 | 12/1995 |
| WO | 2010094985 A1 | 8/2010 |
| WO | 2013057168 A2 | 4/2013 |
| WO | 2022011268 | 1/2022 |

OTHER PUBLICATIONS

Premium Ultrafine (GreenGro Biologicals) <https://www.thegreengro.com/product/premium-ultrafine/> 2017 (Year: 2017).*

Maxwell. "HumiMax" <https://d2j31icv6dlhz6.cloudfront.net/O/16EACbqUqFlemViO7sUS/maxwell-humimax-leaflet-2019.pdf> 2019 (Year: 2019).*

Fulton, John, and Kaylee Port. "Physical properties of granular fertilizers and impact on spreading." Ohio State University, FABE-550.1 (2016). (Year: 2016).*

U S. Utility U.S. Appl. No. 15/878,782, filed Jan. 24, 2018 titled "Fully Water-Soluble Granule Enriched in Humic Acid".

U.S. Utility U.S. Appl. No. 16/210,646, filed Dec. 5, 2018 titled "Process for Making a Semi-Soluble Granule Comprising Rock Phosphate and Humic Acid".

U.S. Utility U.S. Appl. No. 16/266,749, filed Feb. 4, 2019 titled "Potassium Humate Sulfur Compound Granule".

U.S. Utility U.S. Appl. No. 16/387,131, filed Apr. 17, 2019 titled "Process for Making a Composite Granule With Rock Phosphate, Sulfur, and Humic Acid".

Canadian Patent Application No. 3,070,820 filed Feb. 4, 2020 titled "Potassium Humate Sulfur Compound Granule".

Mexican Patent Application No. MX/a/2020/001397 filed Feb. 4, 2020 titled "Potassium Humate Sulfur Compound Granule".

Hiroyuki, Interactions of Methylotrophs with Plants and Other Heterotrophic Bacteria, Microorganisms 2015, 3, 137-151; doi:10.3390/microorganisms3020137, www.mdpi.com/journal/microorganisms, Apr. 2, 2015.

U.S. Appl. No. 16/924,856, filed Jul. 9, 2020 titled Potassium Humate Zinc Sulfate Compound.

U.S. Appl. No. 17/206,053, filed Mar. 18, 2021 titled Process for Making a Semi-Soluble Humic Granule.

United States Patent Office, Notice of Allowance in U.S. Appl. No. 16/210,646 dated Apr. 1, 2021.

United States Patent Office, Final Office Action in U.S. Appl. No. 16/266,749 dated Apr. 5, 2021.

Huey, Lee J., Osumanu H. Ahmed, and Nik MA Majid. "Effects of Extractants on the Yields and Selected Chemical Characteristics of Humic Acids Isolated from Tropical Saprists Peat." American Journal of Applied Sciences 7.7 (2010): 933. (Year: 2010).

Wang et al., Evaluation of Methods of Determining Humic Acids in Nucleic Acid Samples for Molecular Biological Analysis, Biosci. Biotechnol. Biochem., 75(2), 355-357, 2011.

AGN Microbial Selection and Sub-Profiling, Cisbay, www.cisbay.com.

Van Zomeren, Measurement of Humic and Fulvic Acid Concentrations and Dissolution Properties by a Rapid Batch Procedure, Environ. Sci. Technol., 41 (19), pp. 6755-6761, 2007.

Babalola, Beneficial bacteria of agricultural importance, Biotechnol Lett, 32, 1559-1570, 2010.

Comans et al., Concentrations of total dissolved organic carbon and humic and hydrophilic sub-fractions extracted from major Dutch soil types and their relation with soil properties, Geophysical Research Abstractsvol. 15, EGU2013-13841, 2013.

Grow More; Humic/Fulvic Acids, pp. 1-7, Dec. 31, 2003.

Halliday, The relationship between Humalite, Leonardite, and Fertilizers, Black Earth, 2015.

Humic Growth Solutions; Diamond-Grow Organic 100% Water Soluble Spray Dried Humic Acid Powder, pp. 1-2, Jacksonville, FL Dec. 31, 2013.

Topp, Bacteria in agricultural soils: Diversity, role and future perspectives, Canadian Journal of Soil Science, 83, 303-309, 2003.

Javanshah et al., Determination of Humic Acid by Spectrophotometric Analysis in the Soils, International Journal of Advanced Biotechnology and Research (IJBR), vol. 7, pp. 19-23. Special Issue-Apr. 2016.

Lamar et al., A New Standardized Method for Quantification of Humic and Fulvic Acids in Humic Ores and Commercial Products,Journal of AOAC International, 97, 721-730, 2014.

Mineral Logic, LLC, Bioactive Fulvic, Testing Method, Natural Organic Matter Research, 2017.

Myneni, Functional Group Chemistry of Humic Substances, Molecular Environmental Geochemistry Group, The Department of Geosciences, Princeton University, Guyot Hall Princeton, NJ 08544.

Baloach, et al. "Integrated effect of phosphate solubilizing bacteria and humic acid on physiomorphic attributes of maize." International Journal of Current Microbiology and Applied Sciences 3.6 (2014): 549-554.

Sharma, A. K., Seema Wahab, and Rashmi Srivastava, eds. Agriculture diversification: problems and perspectives. IK International Pvt Ltd., 2010.

Jacob, Kenneth Donald, et al. The composition and distribution of phosphate rock with special reference to the United States No. 1488-2016-124804. 1933.

Saint Humic Acid "Potassium humate technical data sheet" <https://www2.slideshare.net/SAINTHUMICACID/potassium-humate-technical-data-sheet-81883698> Nov. 11, 2017 (Year: 2017).

IPCO "Rotoform pastillation for sulphur bentonite" <https://ipco.com/wp-content/uploads/2018/03/IPCO_IP_Sulphur-Bentonite_2018.pdf> Mar. 2018 (Year: 2018).

Canadian Patent Application 3,077,954 filed Apr. 15, 2020 titled Process for Making a Composite Granule With Rock Phosphate, Sulfur, and Humic Acid.

Mexican Patent Applicantion MX/a/2020/004003 filed Apr. 20, 2020 titled Process for Making a Composite Granule With Rock Phosphate, Sulfur, and Humic Acid.

Environmental Fertilisers. "EF Soluble Humate Granules", pp. 1-2. <http://environmentalfertilisers.co.nz/ef-soluble-humate-granules/ > Jun. 21, 2013.

Wikipedia. "Potassium humate". <https://en.wikipedia.org/wiki/Potassium_humate> Mar. 7, 2013.

The Andersons. Products—Andersons Humates | Humic DG. <https://andersonshumates.com/products/ > May 21, 2013.

(56) References Cited

OTHER PUBLICATIONS

Humic DG Product Label, 2016.

Degryse, Fien, et al. "Uptake of elemental or sulfate-S from fall-or spring-applied co-granulated fertilizer by corn-A stable isotope and modeling study." Field crops research 221 (2018): 322-332.

Lindenmayer, R. "Zinc Fertilization: A Review of Scientific Literature." (2007).

U.S. Appl. No. 17/492,917, filed Oct. 4, 2021 titled Potassium Humate Sulfur Compound Granule.

International Search Report and Written Opinion for PCT/US2021/041100 dated Oct. 11, 2021.

ANONYMOUS: "Potassium humate—Wikipedia", May 3, 2019 Retrieved from the Internet: URL: https://en.wikipedia.org/wiki/Potassium_humate [retrieved on Sep. 30, 2021].

Mexican Patent Applicantion MX/a/2022/003257 filed Mar. 17, 2022 titled Process for Making a Semi-Soluble Humic Granule.

\* cited by examiner

US 11,597,688 B1

PROCESS FOR MAKING A FULLY WATER-SOLUBLE GRANULE COMPRISING HUMIC ACID AND A MICROBIAL COMMUNITY COMPOSITION

FIELD OF THE INVENTION

A process such as is described in various embodiments herein relates to a process for making a fully water-soluble granule comprising humic acid and a dormant microbial community composition. Such a granule is useful as an organic aid to crop growth, particularly in applications where solubility is desirable or necessary.

BACKGROUND OF THE INVENTION

Extraction of humic acid and related materials from carbonaceous raw materials (e.g. Humalite, Leonardite, Sub-Bituminous Coal, Menefee, Peat, and the like) has been practiced for years and is accordingly known in the art. Process steps vary, but the process output is generally a particulate material with suboptimal solubility in water.

Suboptimal solubility in water of particulate material enriched in humic acid and related materials presents a problem. Because organic and other producers typically prefer to apply mixtures that contain solvents such as water that are safe and healthful for both plants and workers, there is a need, long-felt by now, for a process for making a fully water-soluble granule enriched in humic acid.

It is known that microbial organisms provide a wide array of beneficial ecosystem services, especially with respect to plant growth and nutrient availability. In particular, it is known that certain bacteria (e.g. plant growth-promoting rhizobacteria) are of agricultural importance for promoting plant growth, suppression of disease causing organisms, and beneficially altering nutrient availability in the soil. Furthermore, it is known that the combination of humic acid and microbial organisms may provide a broad range of benefits to the soil. Conventionally, humic acid and microbial organisms are either applied to the soil separately, or combined and applied in liquid or soluble powder form. Separate application has the primary disadvantage of requiring an additional application step; whereas, use of a liquid form has the primary disadvantages of being difficult to transport and having a shortened shelf life.

Furthermore, since a large percentage of globe relies on dry farming techniques (e.g. non-irrigated farmlands), a combined humic acid and microorganism granule may have the advantages of being easily and evenly applied to the soil in during dry farming operations, which is desirable. Therefore, there is a need to provide a fully-water soluble granule comprising humic acid and a dormant microbial community composition.

SUMMARY OF EMBODIMENTS

The present embodiments provide one or more of the features recited in the appended claims and/or the following features which alone or in any combination, may comprise patentable subject matter.

In a first aspect, a fully water-soluble composite granule is disclosed, where the granule includes: a homogenous powder, where the homogenous power further includes a hydrolyzed humic acid enriched powder and a microbial community composition powder with a plurality of dormant microbial organisms at a ratio of about 1:100 to about 1:5, where the homogenous powder is granulated to form a fully water-soluble composite granule, and where the composite granule is between about 0.5 mm and about 4.5 mm in diameter.

In some embodiments, the plurality of dormant microbial organisms includes at least one species selected from a group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus,* and *Trichoderma*.

In some embodiments, the microbial community composition powder includes a lyophilized microbial powder.

In some embodiments, the composite granule is between about 0.8 mm and about 2.0 mm in diameter. In other embodiments, the composite granule is between about 2.1 mm and about 4.0 mm in diameter.

In some embodiments, at least about 95% of the composite granule dissolves within five minutes when the composite granule is submerged in one liter of water at a temperature of 25 degrees Celsius. In other embodiments, at least about 99% of the composite granule dissolves within five minutes when the composite granule is submerged in one liter of water at a temperature of 25 degrees Celsius. In still other embodiments, at least about 95% of the composite granule dissolves within one minute when the composite granule is submerged in one liter of water at a temperature of 25 degrees Celsius. In still yet other embodiments, at least about 99% of the composite granule dissolves within one minute when the composite granule is submerged in one liter of water at a temperature of 25 degrees Celsius.

In another aspect, a process for making a fully water-soluble granule comprising humic acid and a microbial community composition is described, the process including: obtaining a sample of a carbonaceous substance comprising humic acid and one or more other substances; contacting the sample with an amount of an alkaline mixture, thereby forming an extraction mixture, the extraction mixture consisting essentially of a sludge component, the sludge component comprising, predominantly, the sample, and an extraction component, the extraction component comprising, predominantly, the alkaline mixture; maintaining the sludge component in contact with the extraction component for a period of time sufficient for the extraction component to become relatively enriched in humic acid and the sludge component to become relatively depleted of humic acid; separating the sludge component from the extraction component; spray drying the extraction component, thereby forming a plurality of humic acid enriched powder particles; combining a microbial community composition to the plurality of humic acid enriched powder particles, thereby forming a powder combination; and compacting at least a portion of the powder combination under conditions where the at least a portion of the powder combination, as a result of the compacting, are made into a form of a granule; thereby making a fully water-soluble granule comprising humic acid and a microbial community composition.

In some embodiments, the microbial community composition includes a plurality of microbial species in a dormant and/or endosporic state.

In some embodiments, the microbial community composition includes at least one species selected from the group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus,* and *Trichoderma.*

In some embodiments, the microbial community composition comprises a lyophilized microbial powder.

In some embodiments, the compacting is effected by an apparatus comprising a roller compactor. In other embodiments, the roller compactor maintains a speed of about 8 rpm and wherein the roller compactor exerts a pressure of about 1700 psi. In still other embodiments, the roller compactor does not exceed a temperature of about 130 degrees Fahrenheit.

In some embodiments, the fully water-soluble granule comprising humic acid and a microbial community composition is utilized in a dry granule form. In other embodiments, the fully water-soluble granule is solubilized, thereby forming a fully solubilized solution; and the fully solubilized solution applied to a desired location.

In some embodiments, the powder combination has a ratio of about 1:100 to 1:5 microbial community composition to the plurality of humic acid enriched powder particles.

In yet another aspect, a fully water-soluble granule comprising humic acid and a microbial community composition is made by a process including: obtaining a sample of a carbonaceous substance comprising humic acid and one or more other substances; contacting the sample with an amount of an alkaline mixture, thereby forming an extraction mixture, the extraction mixture consisting essentially of a sludge component, the sludge component comprising, predominantly, the sample, and an extraction component, the extraction component comprising, predominantly, the alkaline mixture; maintaining the sludge component in contact with the extraction component for a period of time sufficient for the extraction component to become relatively enriched in humic acid and the sludge component to become relatively depleted of humic acid; separating the sludge component from the extraction component; drying the extraction component, thereby forming a plurality of humic acid enriched powder particles; combining a microbial community composition to the plurality of humic acid enriched powder particles, thereby forming a powder combination, wherein the powder combination has a ratio of about 1:100 to 1:5 microbial community composition to the plurality of powder particles; and compacting at least a portion of the powder combination under conditions, wherein the at least a portion of the powder combination, as a result of the compacting, are made into a form of a granule; thereby making a fully water-soluble granule comprising humic acid and a microbial community composition.

BRIEF DESCRIPTION OF THE FIGURES

FIG. 2A illustrates composite granules ranging from about 0.8 mm to about 1.0 mm in diameter. FIG. 2B illustrates composite granules ranging from about 1.0 mm to about 1.4 mm in diameter. FIG. 2C illustrates composite granules ranging from about 1.4 mm to about 2.0 mm in diameter. FIG. 2D illustrates composite granules ranging from about 2.0 mm to about 2.8 mm in diameter. FIG. 2E illustrates composite granules ranging from about 2.8 mm to about 4.0 mm in diameter. Each of FIGS. 2A-2E include a United States dime for reference, which has a standard diameter of 17.9 mm.

DETAILED DESCRIPTION

Figure 1:
FIG. 1 is a photographic illustration of an embodiment of fully water-soluble granules comprising humic acid and a microbial community composition described herein.
Figure 2A:
FIGS. 2A-2E are photographic illustrations of embodiments of fully water-soluble granules comprising humic acid and a microbial community composition described herein.
Figure 2B:
Figure 2C:
Figure 2D:
Figure 2E:

A process and composition such as is described in various embodiments herein now will be described more fully hereinafter. A process such as is described in various embodiments herein may, however, be embodied in many different forms and should not be construed as limited to the embodiments set forth herein; rather, these embodiments are provided so that this disclosure will be thorough and complete, and will fully convey the scope of a process such as is described in various embodiments herein to those skilled in the art. As used in this specification and the claims, the singular forms "a," "an," and "the" include plural referents unless the context clearly dictates otherwise. When used in this specification and the claims as an adverb rather than a preposition, "about" means "approximately" and comprises the stated value and every value within 10% of that value; in other words, "about 100%" includes 90% and 110% and every value in between.

When used in this specification and the claims, a "water-soluble granule" or "water-soluble composite granule" refers to a granule that dissolves readily in water under typical conditions of use (e.g. during rainy conditions). Furthermore, when used in this specification and the claims, a "fully water-soluble granule" or "fully water-soluble composite granule" refers to a granule that dissolves readily and entirely in water under typical conditions of use.

When used in this specification and the claims, a product is "enriched in humic acid" if the product possesses a higher concentration of humic acid than a raw material from which the product is made. A component becomes "enriched in humic acid" as the concentration of humic acid in the component increases. A component becomes "depleted of humic acid" as the concentration of humic acid in the component decreases.

When used in this specification and the claims, a "carbonaceous substance comprising humic acid and one or more other substances" refers to a carbonaceous substance that contains humic acid and that also contains one or more other substances other than humic acid. An example is Humalite. An example is lignite. An example is Leonardite.

When used in this specification and the claims, a "dormant" microbial organism refers to a period in a microbial organism's life cycle when metabolic activity is temporarily slowed. Microbial organisms may enter a dormant state when stressful conditions are encountered, such as exposure to the cold, nutrient depletion or starvation, or the like. Dormancy is a reversible state, from which a microbial organism can exit and return to its typical metabolic activity. As a non-limiting example, some organisms (e.g. members of the genus *Bacillus*) may form (or be induced to form) endospores when entering a dormant state. Endospores are tough, non-reproductive, structures produced by a bacterium that function to aid the organism's survival. In some instances, endospores may be resistant to ultraviolet radiation, lysosomes, extreme temperatures, nutrient depletion, and/or chemical disinfectants. As a further non-limiting example, organisms may be induced into a dormant state through lyophilization. Lyophilization is the process of freeze-dying microbial organisms, which includes culturing the desired microorganism, suspending the culture in an appropriate lyophilization medium or buffer, and subjecting the suspended culture to a lyophilization process. Lyophilized microorganisms may then be rehydrated at a desired time.

Aspects of a process such as is described in various embodiments herein are further illustrated by the following examples, which are set forth to illustrate certain aspects of a process such as is described in various embodiments herein and are not to be construed as limiting thereof.

In an example, production of a fully-water soluble composite granule comprising humic acid and a microbial community composition was undertaken as a multi-step process comprising blending of raw material and an alkaline mixture in a blend tank; screening of the blended mixture that was made in the blend tank; drying of the liquid derived from screening of the blended mixture, thereby forming a fine powder; combining this hydrolyzed humic acid enriched powder with a dormant microbial powder; and conversion of the combined powder to form granules.

In an example, a blending of raw material with an alkaline mixture in a blend tank resulted in extraction of humic acid and other humic substances from the raw material. Hot water and caustic potash solution and Humalite were added to a thermally insulated tank in that order and blended. The hot water was at 160-180 degrees Fahrenheit. The caustic potash solution was 45% membrane grade. The mass ratio of hot water to caustic potash solution to Humalite was 73.7:5.8:20.5.

In an example, water, caustic potash solution and Humalite were placed into a thermally insulated tank to form a 42,000 lb mixture, which was then blended. The liquid phase was sampled, and a colorimetric assay for humic acid was performed on each sample, in which the amount of light absorbed was proportional to the concentration of humic acid.

In an example, a blended mixture prepared according to the paragraph immediately above consisted of liquid and sludge. This blended mixture was then pumped by a 3 HP motor to two 200 mesh screeners at a rate of ~40 gal/min (~350 lbs/min). It took ~120 minutes to screen 42000 lbs. The screener allowed liquids and very small particles to be passed through, but not the insoluble sand, clay and humin fraction, also known as sludge. The amount of sludge varied, but typically the sludge was about 5-7% of the total weight of the blended mixture.

In an example, the sludge still possessed some humic content and was given away to local farmers free of charge. The screened humic acid enriched liquid, which had a density of 8.35-9 lb/gallon, was collected in an insulation tank, which had a capacity of 12500 gal. The humic acid enriched liquid was pumped from the insulation tank to a spray dryer firing tank from which it was transferred to a spray dryer.

In an example, a spray dryer system comprised a burner, a dryer, two cyclone separators, a baghouse and a powder hopper. Humic acid enriched liquid was processed at a rate of 14-16 gal/min. Hydraulic pressure-nozzle atomization was used in which liquid was passed through a filter and then through a hydraulic pressure pump. The pressure of the liquid was directly proportional to the force delivered by the hydraulic pressure pump and was generally 1500 psi but ranged from 1300-1700 psi depending on the moisture of the fine powder. The humic acid enriched liquid was then forced through 8 nozzles to break the liquid into fine droplets. Filtered air was passed through a burner where it was heated to 600-650 degrees Fahrenheit. The temperature of the inlet air never exceeded 800 degrees Fahrenheit. The hot air met the liquid droplets in a co-current manner for a time of about 2 seconds. This time was enough to remove more than 85% of the moisture from the dryer to form a humic acid enriched powder, which was collected in a common line. The air emerging out of the dryer still had some particles and was generally at 190-205 degrees Fahrenheit and never exceeded 250 degrees Fahrenheit. Heavier particles were collected using two cyclone separators in series and the lighter particles were collected using a baghouse filter. The hot gas, also called flue gas, was then emitted from the bag house; the hot gas consisted mostly of air and steam at 150-180 degrees Fahrenheit. The temperature of the exhaust never exceeded 250 degrees Fahrenheit. The humic acid enriched powder from the common line was then transferred to a powder hopper. Moisture content of the powder was measured and kept between 11%-13%. When the moisture was below 11%, moisture content was increased in either of two ways, by reducing the temperature of the burner or by operating the hydraulic pressure pump at a higher capacity which in turn increased the flow rate of the liquid. When the moisture was above 13%, moisture content was decreased in either of two ways, by increasing the temperature of the burner or by operating the hydraulic pressure pump at a lower capacity which in turn decreased the flow rate of the liquid. The loose bulk density of the humic acid enriched powder ranged from about 35 to about 42 pounds per cubic foot. The feed particle size distribution of a typical powder sample was as follows: 1.5% of the particles by weight were less than 100 microns; 15% of the particles by weight were less than 200 microns; 35% of the particles by weight were less than 270 microns; 55% of the particles by weight were less than 400 microns.

In an example, the fine humic acid enriched powder may be homogenized with a dormant microbial community composition powder in a ribbon blender for such a time so as to obtain a fine, completely homogenous blend of humic acid enriched powder and dormant microbial community composition powder. The specific microbial community composition may vary based on the end use of the granule. As a non-limiting example, in some instances in may be desirable to include microbial organisms capable of nitrogen fixation; while in other instances, in may be desirable to include organisms capable of bioremediation of the soil. As such, in some circumstances, a commercially available dormant microbial community composition powder may be used; while, in other circumstances, it may be desirable to custom tailor the microbial community composition to the desired end use of the granule. As discussed previously, lyophilization may be used to in order to induce dormancy in the microbial community, microbial community compositions may be lyophilized through use of a shelf lyophilizer, a manifold, or any other method of lyophilization known in the art.

In an example, conversion of the fine combined powder to form the fully water-soluble composite granule comprising humic acid and a dormant microbial community composition was effected by an apparatus comprising a mechanical roller compactor, with pocket rollers at 8 rpm rotation and 1700 psi. Conventionally, the granulation process has required conditions not conducive to the survival of various microorganisms. In contrast, the process described herein results in the survival of the dormant microbial community composition, such that the organism may be rehydrated and return to typical metabolic activity.

Compacted composite granules were blown out pneumatically and screened by means of a vibratory screener to achieve relative uniformity of size distribution. For example, composite granules of 2.1 mm-4.0 mm were prepared for various agricultural uses, and composite granules of 0.8 mm-2.0 mm were prepared for horticultural use. Resulting composite granules allow for easy transport, as well as application in dry farming systems.

Resulting composite granules dissolved readily in water (e.g. rain water in dry farming applications) and have been found to aid plant growth in both agricultural and horticultural applications.

Aspects of a process such as is described in various embodiments herein are further illustrated by the following further examples, which are set forth to illustrate certain aspects of a process such as is described in various embodiments herein and are not to be construed as limiting thereof.

Further example 1. A process for making a fully water-soluble granule comprising humic acid and a microbial community composition, the process comprising:
  obtaining a sample of a carbonaceous substance comprising humic acid and one or more other substances;
  contacting the sample with an amount of an alkaline mixture, thereby forming an extraction mixture, the extraction mixture consisting essentially of a sludge component, the sludge component comprising, predominantly, the sample, and an extraction component, the extraction component comprising, predominantly, the alkaline mixture;
  maintaining the sludge component in contact with the extraction component for a period of time sufficient for the extraction component to become relatively enriched in humic acid and the sludge component to become relatively depleted of humic acid;
  separating the sludge component from the extraction component;
  spray drying the extraction component, thereby forming a plurality of humic acid enriched powder particles;
  combining a microbial community composition to the plurality of humic acid enriched powder particles, thereby forming a powder combination; and
  compacting at least a portion of the powder combination under conditions wherein the at least a portion of the powder combination, as a result of the compacting, are made into a form of a granule;
  thereby making a fully water-soluble granule comprising humic acid and a microbial community composition.

Further example 2. A process according to further example 1, wherein the carbonaceous substance comprises a coal and/or a claystone and/or a mudstone and/or a shale.

Further example 3. A process according to further example 1, wherein the carbonaceous substance comprises a lignite and/or a Leonardite and/or a Humalite.

Further example 4. A process according to further example 1, wherein the carbonaceous substance comprises a Humalite.

Further example 5. A process according to further example 1, wherein the alkaline mixture comprises water.

Further example 6. A process according to further example 1, wherein the alkaline mixture comprises a base.

Further example 7. A process according to further example 1, wherein the alkaline mixture comprises sodium hydroxide or potassium hydroxide.

Further example 8. A process according to further example 1, wherein the alkaline mixture comprises caustic potash solution.

Further example 9. A process according to further example 1, wherein the alkaline mixture comprises, by mass, between about 10 and about 15 parts water, and about 1 part caustic potash solution, wherein the caustic potash solution is 45% membrane grade.

Further example 10. A process according to further example 1, wherein the alkaline mixture comprises, by mass, about 73.7 parts water and about 5.8 parts caustic potash solution, wherein the caustic potash solution is 45% membrane grade.

Further example 11. A process according to further example 1, wherein the mass ratio of the alkaline mixture to the sample is between about 75:25 and about 84:16.

Further example 12. A process according to further example 1, wherein the mass ratio of the alkaline mixture to the sample is between about 78:22 and about 81:13.

Further example 13. A process according to further example 1, wherein the mass ratio of the alkaline mixture to the sample is about 79.5:20.5.

Further example 14. A process according to further example 1, wherein the sludge component is maintained in contact with the extraction component for between about 4 hours and about 12 hours.

Further example 15. A process according to further example 1, wherein the sludge component is maintained in contact with the extraction component for between about 6 hours and about 10 hours.

Further example 16. A process according to further example 1, wherein the sludge component is maintained in contact with the extraction component for about 8 hours.

Further example 17. A process according to further example 1, wherein the sludge component is maintained in contact with the extraction component for a period of time sufficient for the extraction component to possess a humic acid content of at least about 6%.

Further example 18. A process according to further example 1, wherein the sludge component is maintained in contact with the extraction component for a period of time sufficient for the extraction component to possess a humic acid content of at least about 14%.

Further example 19. A process according to further example 1, wherein the sludge component is maintained in contact with the extraction component for a period of time sufficient for the extraction component to possess a humic acid content of at least about 17%.

Further example 20. A process according to further example 1, wherein the sludge component is maintained in contact with the extraction component for a period of time sufficient for the extraction component to possess a humic acid content of at least about 18%.

Further example 21. A process according to further example 1, wherein the separating is effected by filtration.

Further example 22. A process according to further example 1, wherein the separating is effected by sedimentation.

Further example 23. A process according to further example 1, wherein the drying is effected by spray drying.

Further example 24. A process according to further example 1, wherein the drying is effected by spray drying, and wherein the spray drying is characterized by an inlet temperature and an outlet temperature, and wherein the inlet temperature is between about 500 degrees Fahrenheit and about 800 degrees Fahrenheit, and wherein the outlet temperature is between about 150 degrees Fahrenheit and about 250 degrees Fahrenheit.

Further example 25. A process according to further example 1, wherein the drying is effected by spray drying, and wherein the spray drying is characterized by an inlet temperature and an outlet temperature, and wherein the inlet temperature is between about 600 degrees Fahrenheit and about 650 degrees Fahrenheit, and wherein the outlet temperature is between about 150 degrees Fahrenheit and about 180 degrees Fahrenheit.

Further example 26. A process according to further example 1, wherein the plurality of humic acid enriched powder particles is characterized by a moisture content, and wherein the moisture content is between about 9% and about 15%.

Further example 27. A process according to further example 1, wherein the plurality of humic acid enriched powder particles is characterized by a moisture content, and wherein the moisture content is between about 10% and about 14%.

Further example 28. A process according to further example 1, wherein the plurality of humic acid enriched powder particles is characterized by a moisture content, and wherein the moisture content is between about 11% and about 13%.

Further example 29. A process according to further example 1, wherein the plurality of humic acid enriched powder particles is characterized by a loose bulk density, and wherein the loose bulk density is between about 28 and about 49 pounds per cubic foot.

Further example 30. A process according to further example 1, wherein the plurality of humic acid enriched powder particles is characterized by a loose bulk density, and wherein the loose bulk density is between about 31.5 and about 45.5 pounds per cubic foot.

Further example 31. A process according to further example 1, wherein the plurality of humic acid enriched powder particles is characterized by a loose bulk density, and wherein the loose bulk density is between about 35 and about 42 pounds per cubic foot.

Further example 32. A process according to further example 1, wherein the plurality of humic acid enriched powder particles is characterized by a particle size distribution, and wherein, in the particle size distribution, about 1.5% of the particles by weight are less than about 100 microns, about 15% of the particles by weight are less than about 200 microns, about 35% of the particles by weight are less than 270 microns, and about 55% of the particles by weight are less than about 400 microns.

Further example 33. A process according to further example 1, wherein the microbial composition comprises a plurality of microorganisms in a dormant state.

Further example 34. A process according to further example 1, wherein the microbial community composition comprises a lyophilized microbial powder.

Further example 35. A process according to further example 1, wherein the microbial composition comprises a plurality of microorganisms in an endosporic state.

Further example 36. A process according to further example 1, wherein the microbial community composition includes at least one species selected from the group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus*, and *Trichoderma*.

Further example 37. A process according to further example 1, wherein the powder combination has a ratio of about 1:100 to 1:5 microbial community composition to the plurality of humic acid enriched powder particles.

Further example 38. A process according to further example 1, wherein the compacting of the powder combination is effected by an apparatus comprising a roller compactor.

Further example 39. A process according to further example 1, wherein the compacting is effected by an apparatus comprising a roller compactor, and wherein the speed of the roller compactor is about 8 rpm.

Further example 40. A process according to further example 1, wherein the compacting is effected by an apparatus comprising a roller compactor, and wherein the pressure exerted by the roller compactor is about 1700 psi.

Further example 41. A process according to further example 1, wherein the compacting is effected by an apparatus comprising a roller compactor, wherein the speed of the roller compactor is about 8 rpm, and wherein the pressure exerted by the roller compactor is about 1700 psi.

Further example 42. A process according to further example 1, wherein the compacting is effected by an apparatus comprising a roller compactor, wherein the speed of the roller compactor is about 8 rpm, wherein the pressure exerted by the roller compactor is about 1700 psi, and wherein the temperature does not exceed about 130 degrees Fahrenheit.

Further example 43. A process according to further example 1, wherein the compacting conditions do not denature at least a portion of the microbial community composition.

Further example 44. A process according to further example 1, wherein at least a portion of the microbial community composition within the fully water-soluble granule is dormant and may be rehydrated for use.

Further exampled 45. A process according to further example 1, wherein at least about 80% of the microbial community composition is incorporated into the fully water-soluble granule.

Further exampled 46. A process according to further example 1, wherein at least about 90% of the microbial community composition is incorporated into the fully water-soluble granule.

Further exampled 47. A process according to further example 1, wherein at least about 95% of the microbial community composition is incorporated into the fully water-soluble granule.

Further exampled 48. A process according to further example 1, wherein at least about 99% of the microbial community composition is incorporated into the fully water-soluble granule.

Further exampled 49. A process according to further example 1, wherein 100% of the microbial community composition is incorporated into the fully water-soluble granule.

Further example 50. A process according to further example 1, wherein the fully water-soluble granule is between about 0.5 mm and about 4.5 mm.

Further example 51. A process according to further example 1, wherein the fully water-soluble granule is between about 0.8 mm and about 4.0 mm.

Further example 52. A process according to further example 1, wherein the fully water-soluble granule is between about 0.8 mm and about 2.0 mm.

Further example 53. A process according to further example 1, wherein the fully water-soluble granule is between about 2.1 mm and about 4.0 mm.

Further example 54. A process according to further example 1, wherein at least about 75% of the fully water-soluble granule is dissolved in five minutes when the granule is submerged in one liter of water at a temperature of 25 degrees Celsius.

Further example 55. A process according to further example 1, wherein at least about 90% of the fully water-soluble granule is dissolved in five minutes when the granule is submerged in one liter of water at a temperature of 25 degrees Celsius.

Further example 56. A process according to further example 1, wherein at least about 95% of the fully water-soluble granule is dissolved in five minutes when the granule is submerged in one liter of water at a temperature of 25 degrees Celsius.

Further example 57. A process according to further example 1, wherein at least about 99% of the fully water-soluble granule is dissolved in five minutes when the granule is submerged in one liter of water at a temperature of 25 degrees Celsius.

Further example 58. A process according to further example 1, wherein 100% of the fully water-soluble granule is dissolved in five minutes when the granule is submerged in one liter of water at a temperature of 25 degrees Celsius.

Further example 59. A process according to further example 1, wherein at least about 75% of the fully water-soluble granule is dissolved in one minute when the granule is submerged in one liter of water at a temperature of 25 degrees Celsius.

Further example 60. A process according to further example 1, wherein at least about 90% of the fully water-soluble granule is dissolved in one minute when the granule is submerged in one liter of water at a temperature of 25 degrees Celsius.

Further example 61. A process according to further example 1, wherein at least about 95% of the fully water-soluble granule is dissolved in one minute when the granule is submerged in one liter of water at a temperature of 25 degrees Celsius.

Further example 62. A process according to further example 1, wherein at least about 99% of the fully water-soluble granule is dissolved in one minute when the granule is submerged in one liter of water at a temperature of 25 degrees Celsius.

Further example 63. A process according to further example 1, wherein 100% of the fully water-soluble granule is dissolved in one minute when the granule is submerged in one liter of water at a temperature of 25 degrees Celsius.

Further example 64. A process according to further example 1, wherein the process further includes solubilizing the fully water-soluble granule, thereby forming a fully solubilized solution and applying the fully solubilized solution to a desired location.

Further example 65. A process according to further example 1, wherein the process further includes applying the fully-water soluble granule to a desired location.

Aspects of a fully water-soluble composite granule such as is described in various embodiments herein are further illustrated by the following further examples, which are set forth to illustrate certain aspects of a process such as is described in various embodiments herein and are not to be construed as limiting thereof.

Further example 66. A fully water-soluble composite granule comprising humic acid and a microbial community composition, the granule made by a process comprising:
  obtaining a sample of a carbonaceous substance comprising humic acid and one or more other substances;
  contacting the sample with an amount of an alkaline mixture, thereby forming an extraction mixture, the extraction mixture consisting essentially of a sludge component, the sludge component comprising, predominantly, the sample, and an extraction component, the extraction component comprising, predominantly, the alkaline mixture;
  maintaining the sludge component in contact with the extraction component for a period of time sufficient for the extraction component to become relatively enriched in humic acid and the sludge component to become relatively depleted of humic acid;
  separating the sludge component from the extraction component;
  drying the extraction component, thereby forming a plurality of humic acid enriched powder particles;
  combining a microbial community composition to the plurality of humic acid enriched powder particles, thereby forming a powder combination, wherein the powder combination has a ratio of about 1:100 to 1:5 microbial community composition to the plurality of powder particles; and
  compacting at least a portion of the powder combination under conditions, wherein the at least a portion of the powder combination, as a result of the compacting, are made into a form of a granule;
  thereby making a fully water-soluble granule comprising humic acid and a microbial community composition.

Further example 67. A granule according to further example 66, wherein the carbonaceous substance comprises a coal and/or a claystone and/or a mudstone and/or a shale.

Further example 68. A fully water-soluble granule according to further example 66, wherein the carbonaceous substance comprises a lignite and/or a Leonardite and/or a Humalite.

Further example 69. A fully water-soluble granule according to further example 66, wherein the carbonaceous substance comprises a Humalite.

Further example 70. A fully water-soluble granule according to further example 66, wherein the alkaline mixture comprises water.

Further example 71. A fully water-soluble granule according to further example 66, wherein the alkaline mixture comprises a base.

Further example 72. A fully water-soluble granule according to further example 66, wherein the alkaline mixture comprises sodium hydroxide or potassium hydroxide.

Further example 73. A fully water-soluble granule according to further example 66, wherein the alkaline mixture comprises caustic potash solution.

Further example 74. A fully water-soluble granule according to further example 66, wherein the alkaline mixture comprises, by mass, between about 10 and about 15 parts water, and about 1 part caustic potash solution, wherein the caustic potash solution is 45% membrane grade.

Further example 75. A fully water-soluble granule according to further example 66, wherein the alkaline mixture comprises, by mass, about 73.7 parts water and about 5.8 parts caustic potash solution, wherein the caustic potash solution is 45% membrane grade.

Further example 76. A fully water-soluble granule according to further example 66, wherein the mass ratio of the alkaline mixture to the sample is between about 75:25 and about 84:16.

Further example 77. A fully water-soluble granule according to further example 66, wherein the mass ratio of the alkaline mixture to the sample is between about 78:22 and about 81:13.

Further example 78. A fully water-soluble granule according to further example 66, wherein the mass ratio of the alkaline mixture to the sample is about 79.5:20.5.

Further example 79. A fully water-soluble granule according to further example 66, wherein the sludge component is maintained in contact with the extraction component for between about 4 hours and about 12 hours.

Further example 80. A fully water-soluble granule according to further example 66, wherein the sludge component is maintained in contact with the extraction component for between about 6 hours and about 10 hours.

Further example 81. A fully water-soluble granule according to further example 66, wherein the sludge component is maintained in contact with the extraction component for about 8 hours.

Further example 82. A fully water-soluble granule according to further example 66, wherein the sludge component is maintained in contact with the extraction component for a period of time sufficient for the extraction component to possess a humic acid content of at least about 6%.

Further example 83. A fully water-soluble granule according to further example 66, wherein the sludge component is maintained in contact with the extraction component for a period of time sufficient for the extraction component to possess a humic acid content of at least about 14%.

Further example 84. A fully water-soluble granule according to further example 66, wherein the sludge component is maintained in contact with the extraction component for a period of time sufficient for the extraction component to possess a humic acid content of at least about 17%.

Further example 85. A fully water-soluble granule according to further example 66, wherein the sludge component is maintained in contact with the extraction component for a period of time sufficient for the extraction component to possess a humic acid content of at least about 18%.

Further example 86. A fully water-soluble granule according to further example 66, wherein the separating is effected by filtration.

Further example 87. A fully water-soluble granule according to further example 66, wherein the separating is effected by sedimentation.

Further example 88. A fully water-soluble granule according to further example 66, wherein the drying is effected by spray drying.

Further example 89. A fully water-soluble granule according to further example 66, wherein the drying is effected by spray drying, and wherein the spray drying is characterized by an inlet temperature and an outlet temperature, and wherein the inlet temperature passing through a burner heats to between about 400 degrees and about 800 degrees Fahrenheit, and wherein the outlet temperature is between about 150 degrees Fahrenheit and about 250 degrees Fahrenheit.

Further example 90. A fully water-soluble granule according to further example 66, wherein the drying is effected by spray drying, and wherein the spray drying is characterized by an inlet temperature and an outlet temperature, and wherein the inlet temperature is between about 600 degrees Fahrenheit and about 650 degrees Fahrenheit, and wherein the outlet temperature is between about 150 degrees Fahrenheit and about 180 degrees Fahrenheit.

Further example 91. A fully water-soluble granule according to further example 66, wherein the plurality of humic acid enriched powder particles is characterized by a moisture content, and wherein the moisture content is between about 9% and about 15%.

Further example 92. A fully water-soluble granule according to further example 66, wherein the plurality of humic acid enriched powder particles is characterized by a moisture content, and wherein the moisture content is between about 10% and about 14%.

Further example 93. A fully water-soluble granule according to further example 66, wherein the plurality of humic acid enriched powder particles is characterized by a moisture content, and wherein the moisture content is between about 11% and about 13%.

Further example 94. A fully water-soluble granule according to further example 66, wherein the plurality of humic acid enriched powder particles is characterized by a loose bulk density, and wherein the loose bulk density is between about 28 and about 49 pounds per cubic foot.

Further example 95. A fully water-soluble granule according to further example 66, wherein the plurality of humic acid enriched powder particles is characterized by a loose bulk density, and wherein the loose bulk density is between about 31.5 and about 45.5 pounds per cubic foot.

Further example 96. A fully water-soluble granule according to further example 66, wherein the plurality of humic acid enriched powder particles is characterized by a loose bulk density, and wherein the loose bulk density is between about 35 and about 42 pounds per cubic foot.

Further example 97. A fully water-soluble granule according to further example 66, wherein the plurality of humic acid enriched powder particles is characterized by a particle size distribution, and wherein, in the particle size distribution, about 1.5% of the particles by weight are less than about 100 microns, about 15% of the particles by weight are less than about 200 microns, about 35% of the particles by weight are less than 270 microns, and about 55% of the particles by weight are less than about 400 microns.

Further example 98 A fully water-soluble granule according to further example 66, wherein the microbial composition comprises a plurality of microorganisms in a dormant state.

Further example 99. A fully water-soluble granule according to further example 66, wherein the microbial community composition comprises a lyophilized microbial powder.

Further example 100. A fully water-soluble granule according to further example 66, wherein the microbial composition comprises a plurality of microorganisms in an endosporic state.

Further example 101. A fully water-soluble granule according to further example 66, wherein the microbial community composition includes at least one species selected from the group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus*, and *Trichoderma*.

Further example 102. A fully water-soluble granule according to further example 66, wherein the powder combination has a ratio of about 1:100 to 1:5 microbial community composition to the plurality of humic acid enriched powder particles.

Further example 103. A fully water-soluble granule according to further example 66, wherein the compacting is effected by an apparatus comprising a roller compactor.

Further example 104. A fully water-soluble granule according to further example 66, wherein the compacting is effected by an apparatus comprising a roller compactor, and wherein the speed of the roller compactor is about 8 rpm.

Further example 105. A fully water-soluble granule according to further example 66, wherein the compacting is effected by an apparatus comprising a roller compactor, and wherein the pressure exerted by the roller compactor is about 1700 psi.

Further example 106. A fully water-soluble granule according to further example 66, wherein the compacting is effected by an apparatus comprising a roller compactor, wherein the speed of the roller compactor is about 8 rpm, and wherein the pressure exerted by the roller compactor is about 1700 psi.

Further example 107. A fully water-soluble granule according to further example 66, wherein the compacting is effected by an apparatus comprising a roller compactor, wherein the speed of the roller compactor is about 8 rpm, wherein the pressure exerted by the roller compactor is about 1700 psi, and wherein the temperature does not exceed about 130 degrees Fahrenheit.

Further example 108. A fully water-soluble granule according to further example 66, wherein the compacting conditions do not denature at least a portion of the microbial community composition.

Further example 109. A fully water-soluble granule according to further example 66, wherein at least a portion of the microbial community composition within the granule is dormant and may be rehydrated for use.

Further exampled 110. A fully water-soluble granule according to further example 66, wherein at least about 80% of the microbial community composition is incorporated into the granule.

Further exampled 111. A fully water-soluble granule according to further example 66, wherein at least about 90% of the microbial community composition is incorporated into the granule.

Further exampled 112. A fully water-soluble granule according to further example 66, wherein at least about 95% of the microbial community composition is incorporated into the granule.

Further exampled 113. A fully water-soluble granule according to further example 66, wherein at least about 99% of the microbial community composition is incorporated into the granule.

Further exampled 114. A fully water-soluble granule according to further example 66, wherein 100% of the microbial community composition is incorporated into the granule.

Further example 115. A fully water-soluble granule according to further example 66, wherein the granule is between about 0.5 mm and about 4.5 mm.

Further example 116. A fully water-soluble granule according to further example 66, wherein the granule is between about 0.8 mm and about 4.0 mm.

Further example 117. A fully water-soluble granule according to further example 66, wherein the granule is between about 0.8 mm and about 2.0 mm.

Further example 118. A fully water-soluble granule according to further example 66, wherein the granule is between about 2.1 mm and about 4.0 mm.

Further example 119. A fully water-soluble granule according to further example 66, wherein at least about 75% of the granule is dissolved in five minutes when the granule is submerged in one liter of water at a temperature of 25 degrees Celsius.

Further example 120. A fully water-soluble granule according to further example 66, wherein at least about 90% of the granule is dissolved in five minutes when the granule is submerged in one liter of water at a temperature of 25 degrees Celsius.

Further example 121. A fully water-soluble granule according to further example 66, wherein at least about 95% of the granule is dissolved in five minutes when the granule is submerged in one liter of water at a temperature of 25 degrees Celsius.

Further example 122. A fully water-soluble granule according to further example 66, wherein at least about 99% of the granule is dissolved in five minutes when the granule is submerged in one liter of water at a temperature of 25 degrees Celsius.

Further example 123. A fully water-soluble granule according to further example 66, wherein 100% of the granule is dissolved in five minutes when the granule is submerged in one liter of water at a temperature of 25 degrees Celsius.

Further example 124. A fully water-soluble granule according to further example 66, wherein at least about 75% of the granule is dissolved in one minute when the granule is submerged in one liter of water at a temperature of 25 degrees Celsius.

Further example 125. A fully water-soluble granule according to further example 66, wherein at least about 90% of the granule is dissolved in one minute when the granule is submerged in one liter of water at a temperature of 25 degrees Celsius.

Further example 126. A fully water-soluble granule according to further example 66, wherein at least about 95% of the granule is dissolved in one minute when the granule is submerged in one liter of water at a temperature of 25 degrees Celsius.

Further example 127. A fully water-soluble granule according to further example 66, wherein at least about 99% of the granule is dissolved in one minute when the granule is submerged in one liter of water at a temperature of 25 degrees Celsius.

Further example 128. A fully water-soluble granule according to further example 66, wherein 100% of the granule is dissolved in one minute when the granule is submerged in one liter of water at a temperature of 25 degrees Celsius.

Further example 129. A fully water-soluble granule according to further example 66, wherein the fully water-soluble granule is solubilized forming a fully solubilized solution, and the fully solubilized solution applied to a desired location.

Further example 130. A fully water-soluble granule according to further example 66, wherein the fully-water soluble granule is applied to a desired location, such as agricultural soil.

Aspects of a composite granule comprising humic acid and a microbial community composition such as is described in various embodiments herein are further illustrated by the following further example, which is set forth to illustrate certain aspects of a process such as is described in various embodiments herein and are not to be construed as limiting thereof.

Further example 131. A fully water-soluble composite granule comprising:
a homogenous power,
wherein the homogenous power comprises a hydrolyzed humic acid enriched powder and a microbial community composition powder comprising a plurality of dormant microbial organisms at a ratio of about 1:100 to about 1:5,
wherein the homogenous powder is granulated to form a fully water-soluble composite granule,
wherein the composite granule is between about 0.5 mm and about 4.5 mm in diameter.

Further example 132. A composite granule of further example 131, wherein the plurality of dormant microbial organisms includes at least one species selected from the group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus*, and *Trichoderma*.

Further example 132. A composite granule of further example 131, wherein the microbial community composition powder includes a lyophilized microbial powder.

Further example 133. A composite granule according to further example 131, wherein at least of a portion of the plurality of dormant microbial organisms within the composite granule may be rehydrated for use.

Further example 134. A composite granule according to further example 131, wherein the composite granule is between about 0.5 mm and about 4.5 mm.

Further example 135. A composite granule according to further example 131, wherein the composite granule is between about 0.8 mm and about 4.0 mm.

Further example 136. A composite granule according to further example 131, wherein the composite granule is between about 0.8 mm and about 2.0 mm.

Further example 137. A composite granule according to further example 131, wherein the composite granule is between about 2.1 mm and about 4.0 mm.

Further example 138. A composite granule according to further example 131, wherein at least about 75% of the composite granule is dissolved in five minutes when the composite granule is submerged in one liter of water at a temperature of 25 degrees Celsius.

Further example 139. A composite granule according to further example 131, wherein at least about 90% of the composite granule is dissolved in five minutes when the composite granule is submerged in one liter of water at a temperature of 25 degrees Celsius.

Further example 140. A composite granule according to further example 131, wherein at least about 95% of the composite granule is dissolved in five minutes when the composite granule is submerged in one liter of water at a temperature of 25 degrees Celsius.

Further example 141. A composite granule according to further example 131, wherein at least about 99% of the composite granule is dissolved in five minutes when the composite granule is submerged in one liter of water at a temperature of 25 degrees Celsius.

Further example 142. A composite granule according to further example 131, wherein 100% of the composite granule is dissolved in five minutes when the composite granule is submerged in one liter of water at a temperature of 25 degrees Celsius.

Further example 143. A composite granule according to further example 131, wherein at least about 75% of the composite granule is dissolved in one minute when the composite granule is submerged in one liter of water at a temperature of 25 degrees Celsius.

Further example 144. A composite granule according to further example 131, wherein at least about 90% of the composite granule is dissolved in one minute when the composite granule is submerged in one liter of water at a temperature of 25 degrees Celsius.

Further example 145. A composite granule according to further example 131, wherein at least about 95% of the composite granule is dissolved in one minute when the composite granule is submerged in one liter of water at a temperature of 25 degrees Celsius.

Further example 146. A composite granule according to further example 131, wherein at least about 99% of the composite granule is dissolved in one minute when the composite granule is submerged in one liter of water at a temperature of 25 degrees Celsius.

Further example 147. A composite granule according to further example 131, wherein 100% of the composite granule is dissolved in one minute when the composite granule is submerged in one liter of water at a temperature of 25 degrees Celsius.

Further example 148. A plurality of composite granules according to further example 131 are illustrated in FIG. 1. Generally the hydrolyzed humic acid enriched powder is dark in color, for example black or brown; while the microbial community composition powder is generally light in color, for example white. Therefore, the homogenous power and resulting granules comprises both dark and light portions, as illustrated in FIG. 1. Furthermore, the respective portions of the resulting composited granule are substantially inseparable.

Further example 149. A plurality of composite granules according to further example 131 are illustrated in FIGS. 2A-2E. As evident by FIGS. 2A-2E the composite granules may generally vary in shape and size, and in some instances varying sizes and shapes may be utilized for different purposes. For example, in some instances smaller composite granules (e.g. about 0.8 to about 1.8 mm in diameter), such as those illustrated in FIGS. 2A-2C, may be utilized in turf applications (e.g. on golf courses, lawn maintenance). In other instances, larger composite granules (e.g. about 2.0 to about 4 mm in diameter), such as those illustrated in FIG. 2D-2E, may be utilized in agricultural applications. However, it is to be understood that these examples are for illustrative purposes only and are non-limiting.

Further example 150. A plurality of composite granules according to further example 131 were subjected to crush strength testing. The composite granules were separated by size, with composite granules ranging from about 0.8 to 1.8 mm in diameter being tested together and composite granules ranging from about 2.0 to about 4 mm in diameter being tested together. A total of ten (10) replicates of crush strength testing were conducted, with Tables 1 and 2 illustrating the results for the composite granules ranging from about 0.8 to 1.8 mm in diameter and the composite granules ranging from about 2.0 to about 4.0 mm in diameter, respectively.

SGN, or Size Guide Number is a standard measurement of the diameter, as expressed in millimeters×100, of granules based on the median within the batch. As illustrated in Table 1, the crush strength measurements of the composite granules ranging from about 0.8 mm to 1.9 mm in diameter range from about 0.1 psi to about 3.0 psi, with an average crush strength of about 0.378 psi. The crush strength measurements of the composite granules ranging from about 2.0 to 4.0 mm in diameter range from about 0.1 psi to about 8.0 psi, as illustrated in Table 2. The average crush strength of the composite granules ranging from about 2.0 to 4.0 mm in diameter is about 3.8 psi. However, it is to be understood that these examples are for illustrative purposes only and are non-limiting, in some instances the crush strength of a composite granule consistent with the description herein may range anywhere from 0.1 psi to 10 psi.

TABLE 1

| SGN | % Vol. | Avg. SGN | CT 1 | CT 2 | CT 3 | CT 4 | CT 5 | CT 6 | CT 7 | CT 8 | CT 9 | CT 10 |
|---|---|---|---|---|---|---|---|---|---|---|---|---|
| 280-340-400 | 0.0% | 110 | — | — | — | — | — | — | — | — | — | — |
| 200-240-280 | 0.0% |  | — | — | — | — | — | — | — | — | — | — |
| 140-170-200 | 20% |  | 0.0 | 0.25 | 0.1 | 0.1 | 0.0 | 3.0 | .25 | 0.0 | 0.5 | 0.45 |
| 100-120-140 | 30% |  | 0.1 | 0.5 | 0.25 | 0.3 | 1.0 | 2.0 | 1.25 | 0.1 | 1.0 | 0.5 |
| 60-80-100 | 50% |  | 0.25 | 0.15 | 0.15 | 0.25 | 0.0 | 0.0 | 0.1 | 0.2 | 0.2 | 0.2 |

TABLE 2

| SGN | % Vol. | Avg. SGN | CT 1 | CT 2 | CT 3 | CT 4 | CT 5 | CT 6 | CT 7 | CT 8 | CT 9 | CT 10 |
|---|---|---|---|---|---|---|---|---|---|---|---|---|
| 280-340-400 | 75% | 339 | 1.0 | 4.5 | 8.0 | 2.5 | 6.5 | 3.0 | 3.5 | 3.0 | 6.0 | 5.0 |
| 200-240-280 | 25% |  | 3.5 | 2.0 | 2.5 | 2.5 | 1.5 | 0.0 | 0.0 | 0.0 | 3.5 | 1.0 |
| 140-170-200 | 0.0% |  | — | — | — | — | — | — | — | — | — | — |
| 100-120-140 | 0.0% |  | — | — | — | — | — | — | — | — | — | — |
| 60-80-100 | 0.0% |  | — | — | — | — | — | — | — | — | — | — |

Further example 151. A composite granule according to further example 131, wherein the composite granule is solubilized forming a fully solubilized solution, and the fully solubilized solution applied to a desired location.

Further example 152. A composite granule according to further example 131, wherein the composite granule is applied to a desired location, such as agricultural soil.

Many modifications and other embodiments of a process such as is described in various embodiments herein will come to mind to one skilled in the art to which this disclosed process pertains having the benefit of the teachings presented in the foregoing description. Therefore, it is to be understood that a process such as is described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A fully water soluble composite granule comprising:
    a homogenous powder, wherein the homogenous powder comprises:
        a hydrolyzed humic acid enriched powder extracted from leonardite or humalite with an alkaline mixture and;
        a microbial community composition powder comprising a plurality of dormant microbial organisms at a ratio of about 1:100 to about 1:5;
    wherein the homogenous powder is granulated to form a fully water soluble composite granule such that at least 95% of the fully water soluble composite granule dissolves within five minutes when the fully water soluble composite granule is submerged in one liter of water at a temperature of 25 degrees Celsius;
    wherein the fully water soluble composite granule is between about 0.5 mm and about 4.5 mm in diameter.

2. The fully water soluble composite granule of claim 1, wherein the plurality of dormant microbial organisms includes at least one species selected from the group of genera consisting of: *Acetobacter, Agrobacterium, Aquifex, Arthrobacter, Azoarcus, Azorhizobium, Azospirillum, Azotobacter, Bacillus, Beijerinckia, Burkholderia, Chlorobium, Chloroflexus, Chryseobacterium, Enterococcus, Escherichia, Flavobacterium, Flexibacter, Frankia, Gloeobacter, Gluconacetobacter, Halobacterium, Herbaspirillum, Lactobacillus, Leptonema, Mycobacterium, Paenibacillus, Phyllobacterium, Planctomyces, Pseudomonas, Rhizobia, Rhizobium, Rickettsia, Rhodocyclus, Sinorhizobium, Sphingomonas, Streptomyces, Synechococcus Thermotoga, Thermus*, and *Trichoderma*.

3. The fully water soluble composite granule of claim 1, wherein the microbial community composition powder includes a lyophilized microbial powder.

4. The fully water soluble composite granule of claim 1, wherein the fully water soluble composite granule is between about 0.8 mm and about 2.0 mm in diameter.

5. The fully water soluble composite granule of claim 1, wherein the fully water soluble composite granule is between about 2.1 mm and about 4.0 mm in diameter.

6. The fully water soluble composite granule of claim 1, wherein at least about 99% of the fully water soluble composite granule dissolves within five minutes when the fully water soluble composite granule is submerged in one liter of water at a temperature of 25 degrees Celsius.

7. The fully water soluble composite granule of claim 1, wherein at least about 95% of the fully water soluble composite granule dissolves within one minute when the fully water soluble composite granule is submerged in one liter of water at a temperature of 25 degrees Celsius.

8. The fully water soluble composite granule of claim 1, wherein at least about 99% of the fully water soluble composite granule dissolves within one minute when the fully water soluble composite granule is submerged in one liter of water at a temperature of 25 degrees Celsius.

9. The fully-water soluble granule of claim 1, wherein the fully water soluble composite granule has a crush strength between about 0.1 psi to about 4.0 psi.

10. A fully water soluble granule comprising humic acid and a microbial community composition, the fully water soluble granule made by a process comprising:

obtaining a sample of a carbonaceous substance comprising humic acid and one or more other substances;

contacting the sample with an amount of an alkaline mixture, thereby forming an extraction mixture, the extraction mixture consisting essentially of a sludge component, the sludge component comprising, predominantly, the sample, and an extraction component, the extraction component comprising, predominantly, the alkaline mixture;

maintaining the sludge component in contact with the extraction component for a period of time sufficient for the extraction component to become relatively enriched in humic acid and the sludge component to become relatively depleted of humic acid;

separating the sludge component from the extraction component;

drying the extraction component, thereby forming a plurality of humic acid enriched powder particles, wherein the plurality of humic acid enriched particles has a moisture content of about 9% to about 15% and a loose bulk density between about 28 and 49 pounds per cubic feet;

combining the microbial community composition to the plurality of humic acid enriched powder particles, thereby forming a powder combination, wherein the powder combination has a ratio of about 1:100 to 1:5 microbial community composition to the plurality of humic acid enriched powder particles; and compacting at least a portion of the powder combination under conditions, wherein the at least a portion of the powder combination, as a result of the compacting, are made into a form of a granule;

thereby making a fully water soluble granule comprising humic acid and a microbial community composition, wherein at least 95% of the fully water soluble composite granule dissolves within five minutes when the fully water soluble composite granule is submerged in one liter of water at a temperature of 25 degrees Celsius.

* * * * *